Figure 1:
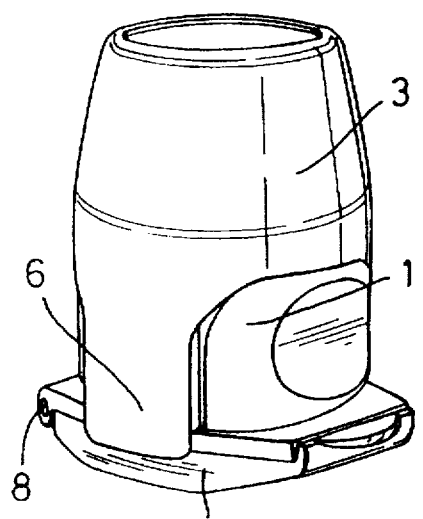

US005787881A

United States Patent [19]
Chawla

[11] Patent Number: 5,787,881
[45] Date of Patent: Aug. 4, 1998

[54] INHALATION DEVICE

[75] Inventor: Brindra Paul Singh Chawla, Nottingham, Great Britain

[73] Assignee: Fisons plc, Suffolk, Great Britain

[21] Appl. No.: 789,073

[22] Filed: Feb. 3, 1997

Related U.S. Application Data

[63] Continuation of Ser. No. 507,405, filed as PCT/GB94/00388 Feb. 28, 1994 published as WO94/19041, Sep. 1, 1994, abandoned.

[30] Foreign Application Priority Data

Feb. 27, 1993 [GB] United Kingdom .............. 9304011
Jun. 5, 1993 [GB] United Kingdom .............. 9311646

[51] Int. Cl.[6] ........................................ A61M 15/00
[52] U.S. Cl. ........................... 128/203.15; 128/203.21
[58] Field of Search ..................... 128/203.15, 203.21; 604/58

[56] References Cited

U.S. PATENT DOCUMENTS

| | | | |
|---|---|---|---|
| 4,069,819 | 1/1978 | Valentini et al. | 128/203.21 |
| 4,841,964 | 6/1989 | Hurka et al. | 604/58 |
| 5,033,463 | 7/1991 | Cocozza | 128/203.21 |
| 5,309,900 | 5/1994 | Knoch et al. | 128/200.14 |
| 5,349,947 | 9/1994 | Newhouse et al. | 128/203.21 |
| 5,429,122 | 7/1995 | Zanen et al. | 128/203.15 |
| 5,476,093 | 12/1995 | Lankinen | 128/203.15 |
| 5,560,490 | 10/1996 | Chawla | 206/539 |
| 5,596,982 | 1/1997 | Blaha-Schnabel | 128/203.15 |

FOREIGN PATENT DOCUMENTS

| | | |
|---|---|---|
| 0 333 334 | 9/1989 | European Pat. Off. . |
| 0 385 156 | 9/1990 | European Pat. Off. . |
| 0385156 | 9/1990 | European Pat. Off. . |
| 0506293 | 9/1992 | European Pat. Off. . |
| 2 264 563 | 10/1975 | France . |
| 9119524 | 12/1991 | WIPO . |

*Primary Examiner*—Aaron J. Lewis
*Attorney, Agent, or Firm*—McAulay Fisher Nissen Goldberg & Kiel, LLP

[57] ABSTRACT

A device for the administration of powdered inhalation medicament contained initially in a capsule having at least one aperture formed therein, comprising a swirl chamber (1) adapted to receive the medicament capsule; a mouthpiece (2) communicating with the swirl chamber (1) and separated therefrom by a grid (4); at least one air inlet (5) in tangential communication with the swirl chamber (1) whereby air can be drawn through the device via the mouthpiece (2) to cause a swirling air flow through the swirl chamber (1); and a cover member (7), having a continuous substantially planar inner surface, provided on the base of the swirl chamber (1) remote from the mouthpiece (2); said cover (7) being moveable between a first position in which the capsule can be inserted into the swirl chamber (1) and a second position in which the capsule is retained in the swirl chamber (1) and rotates upon air being drawn through the device, thereby dispensing the medicament contained therein.

11 Claims, 2 Drawing Sheets

INHALATION DEVICE

This is a continuation of application Ser. No. 08/507,405, filed Oct. 30, 1995, now abandoned, which, in turn, is 371 application of PCT application PCT/GB94/00388 filed Feb. 28, 1994 published as WO94/19041, Sep. 1, 1994.

This invention relates to an inhalation device, in particular to an inhalation device for use with pre-pierced capsules of dry powder medicament.

The administration of inhalation medicaments in dry powder form is well known. Powdered medicament is often supplied in capsules which are loaded into a dispensing device wherein the medicament is released from the capsule then inhaled by the patient.

Powdered medicament contained in a capsule may be dispensed using the device known as the SPINHALER™. This device comprises a housing which retains an individual capsule of medicament which is pierced in situ thus releasing the medicament for inhalation. This device has the disadvantage that small fragments of the capsule may be produced during the opening process which could be inhaled by the patient. Furthermore, the design of piercing mechanism may limit the device to use with medicament capsules of only one size.

European Patent Application 0333334 discloses a device for the administration of medicament from capsules in which the capsule is pierced prior to it's insertion in a dispensing chamber by pushing it onto a pin located in a recess in the base of the dispensing chamber. This device suffers from the disadvantage that it is only possible to pierce one end of the capsule at a time. Thus if it is desired to pierce the capsule at both ends to assist the release of medicament, the piercing procedure must be repeated with the possibility of losing medicament from the first aperture whilst the second is being formed. Furthermore, the recess provided in the base of the dispensing chamber provides an area in which medicament can become trapped possibly reducing the dose administered to the patient and/or making cleaning the device more difficult.

Pre-pierced medicament capsules, i.e. capsules the walls of which are provided with one or more apertures during manufacture, are known. European Patent Application 0385156 discloses a disposable inhaler containing a single pre-pierced capsule. However, this device suffers from the drawback that it may be necessary to carry several separate devices in order to provide a day's supply of medicament. It is also wasteful since the device cannot be refilled and is thus discarded after only one use.

We have now devised an improved inhalation device which overcomes or substantially mitigates the disadvantages of the prior art devices described above.

According to the invention there is provided a device for the administration of powdered inhalation medicament contained initially in a capsule having at least one aperture formed therein, said device comprising a swirl chamber adapted to receive the medicament capsule; a mouthpiece communicating with the swirl chamber and separated therefrom by a grid; at least one air inlet in tangential communication with the swirl chamber whereby air can be drawn through the device via the mouthpiece to cause a swirling air flow through the swirl chamber; and a cover member, having a continuous substantially planar inner surface, provided on the base of the swirl chamber remote from the mouthpiece; said cover being moveable between a first position in which the capsule can be inserted into the swirl chamber and a second position in which the capsule is retained in the swirl chamber and rotates upon air being drawn through the device, thereby dispensing the medicament contained therein.

The cover member may be removably attached to the base of the swirl chamber remote from the mouthpiece, e.g. by a snap-fit or screw-threaded engagement.

Alternatively, the cover member may be slidably attached to the base of the swirl chamber to provide access thereto. However, we prefer the cover member to be in hinged engagement with the base of the swirl chamber, pivotal movement about the hinge allowing the cover to move between the first and second positions. When the cover member is in hinged engagement with the swirl chamber the cover member is preferably adapted to resiliently engage a flange on the swirl chamber at a position remote from the hinge. This resilient engagement ensuring that, when in the second position, the cover member remains closed.

The cover member may be made of a transparent material, thus allowing the patient to readily determine if all the medicament contained in the capsule has been inhaled.

When the cover member is in the second position the continuous substantially planar inner surface of the cover member defines the base of the swirl chamber. The continuous substantially planar surface of the cover member provides an effective seal at the base of the swirl chamber thus preventing the escape of medicament. It also facilitates rotation of the capsule within the swirl chamber.

The device according to the invention may have any practicable number of air inlets in tangential communication with the swirl chamber. We prefer the device to have two air inlets in tangential communication with the swirl chamber. The air inlets are preferably spaced at regular intervals around the swirl chamber.

The mouthpiece of the device may also be provided with a removable cover to help prevent the ingress of dirt and moisture between uses. When the device is provided with a mouthpiece cover it is preferably adapted to cover the both the mouthpiece and the air inlet(s) communicating with the swirl chamber. The mouthpiece cover is preferably provided with protruding element(s) adapted to cover the air inlet(s).

The device according to the invention can be used in a manner which depends only upon the inspiration of the patient to achieve dispersion of the medicament contained in the capsule. It can also be used in a positive gas assisted manner in which an external source of gas, e.g. air, is used to assist rotation of the capsule in the swirl chamber. The external source of gas may be provided manually or electrically, using, for example, a compressed gas cylinder or air compressor. The use of the device in a gas assisted manner may be particularly useful for patients who have low inspiration rates, e.g. infants, the elderly or patients at a critical stage of an asthma attack.

The capsules for use in the device according to the invention may be made from any material in which apertures may be formed, suitable materials include hard or soft gelatin, polystyrene, nylons, polyalkylenes such as polyethylene, cellulose, alkyl cellulose and acetate polymers.

The capsules may be of any shape but are preferably cylindrical. The capsules may contain one or more apertures, e.g. 1 to 6, and especially 2 apertures. The apertures may be situated in any portion of the capsule body. However, when the capsules are cylindrical we prefer them to have an aperture situated at the end of the capsule and more preferably at both ends of the capsule.

The capsule apertures may be of any shape, e.g. square, rectangular, oval, or preferably circular. When the apertures are circular they may have a diameter of between 0.50 and 1.20 mm, preferably from 0.50 to 1.01 mm, more preferably from 0.76 to 1.01 mm and especially 0.81 mm. When the capsule contains more then one aperture then the apertures may have the same or different dimensions.

The method used for forming the capsule apertures will be dependent upon the size, shape and position of the apertures, any conventional techniques known per se may be employed. When a circular or oval aperture is required a cutting tool may be used; alternatively laser light may be employed or a hot needle. When a square or rectangular aperture is required a cutting tool with an inclined terminal face may be employed.

The capsules for use in the device according to the invention may be provided in a blister-pack adapted to seal the capsule aperture(s) until they are removed from the pack, as described in International Patent Application PCT/GB93/01909.

Although the device according to the invention has thus far been described for use in oral inhalation of medicaments, it is also suitable for the administration of nasal medicaments by inhalation. The necessary adaptation for this mode of administration will be readily apparent to those skilled in the art and may take the form of an elongate air passage adapted for insertion into the nostril rather than a mouthpiece.

The device may be used for dispensing any medicament which is conventionally administered by inhalation to the lung or the nose. Such medicaments include drugs for use in the prophylactic or remedial treatment of reversible obstructive airways disease. Specific active ingredients which may be mentioned include salts of cromoglycic acid, e.g. sodium cromoglycate; salts of nedocromil, e.g. nedocromil sodium; inhaled steroids such as beclomethasone dipropionate, tipredane, budesonide and fluticasone; anticholinergic agents such as ipratropium bromide; bronchodilators, e.g. salmeterol, salbutamol, reproterol, terbutaline, isoprenaline and fenoterol, and salts thereof. If desired a mixture of active ingredients, for example, a mixture of sodium cromoglycate and a bronchodilator, such as salbutamol, reproterol, isoprenaline, terbutaline, fenoterol or a salt of any one thereof, may be used.

Other active ingredients that may be mentioned include antihistamines, e.g. clemastine, pentamidine and salts thereof, acetyl-β-methylcholine bromide; peptide hormones, e.g. insulin and amylin; bradykinin antagonists; $PLA_2$ inhibitors; PAF antagonists; lipoxygenase inhibitors; leukotriene antagonists; CNS active drugs, e.g. NMDA antagonists, glutamate antagonists, CCK agonists and antagonists; macrolide compounds, e.g. FK 506, rapamycin, cyclosporin and structurally related compounds; vitamins; vaccines, e.g. MMR vaccine and polio vaccine; and vectors for gene therapy, e.g. plasmids containing genes intended to correct genetic disorders such as cystic fibrosis.

The powdered medicament will generally be administered as a composition including one or more additional pharmaceutically acceptable additives, e.g. a solid carrier of larger particle size. The solid pharmaceutically acceptable carrier will generally be a non-toxic material chemically inert to the inhalation medicament but may, if so desired, also comprise larger particles of the inhalation medicament. Examples of carriers which may be used in the composition include a dextran, mannitol and, preferably, lactose. A particularly preferred carrier is crystalline lactose.

The powdered medicament may also be formulated as a so-called "pelletised" composition, i.e. as soft pellets of diameter greater than 30 μm, each pellet comprising a plurality of individual particles loosely held together such that upon inhalation the pellets disintegrate to the constituent particles. Pelletised compositions may be prepared according to the method described in GB 1520247.

The particular formulation of powdered medicament contained in the capsule will, of course, depend upon the nature of the active ingredient.

The amount of powdered medicament contained in the capsule will depend on the desired dosage and the potency of the active ingredient, but will generally be from about 10 μg to 50 mg, e.g. 20 mg.

According to a further aspect of the invention there is provided a method for administering powdered inhalation medicament contained initially in a capsule having at least one aperture formed therein, which comprises inserting the capsule in a device consisting of a swirl chamber adapted to receive the medicament capsule; a mouthpiece communicating with the swirl chamber and separated therefrom by a grid; at least one air inlet in tangential communication with the swirl chamber whereby air can be drawn through the device via the mouthpiece to cause a swirling air flow through the chamber; and a cover member provided on the base of the swirl chamber remote from the mouthpiece, said cover being moveable between a first position in which a capsule can be inserted into the swirl chamber and a second position in which the capsule is retained in the swirl chamber, and drawing air through the device, such that the capsule rotates in the swirl chamber thereby dispensing the medicament contained therein.

The device according to the invention has advantages over known inhalation devices in that the medicament capsules do not need to be individually pierced by hand; the risk of capsule fragments being inhaled by the patient is substantially reduced; it is safe since there is no sharp piercing mechanism which could cause accidental injury to the patient, it is suitable for the administration of a wide variety of inhalation medicaments which may be contained in capsules of varying sizes; it gives improved capsule emptying; it is of a more compact design; manufacture of the device is considerably simplified since no capsule opening mechanism is required; it is easy to clean; and, since the device contains no internal moving parts, it is less prone to malfunction and therefore may have an extended lifetime.

Figure 3:
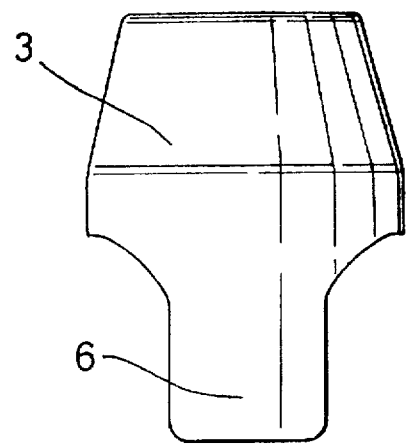
Figure 3:
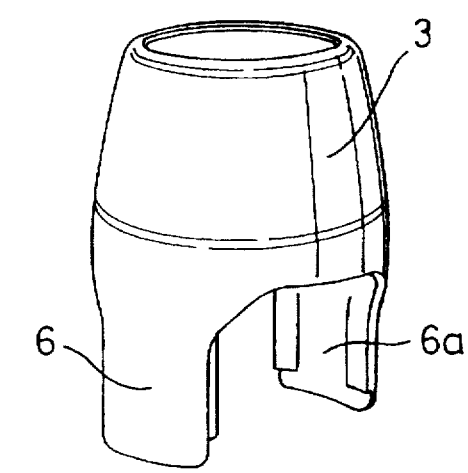
Figure 3:
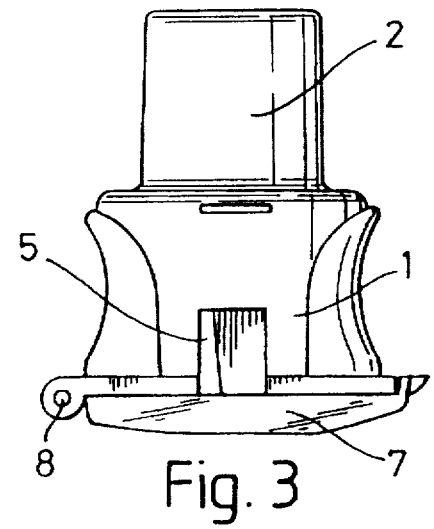
Figure 2:
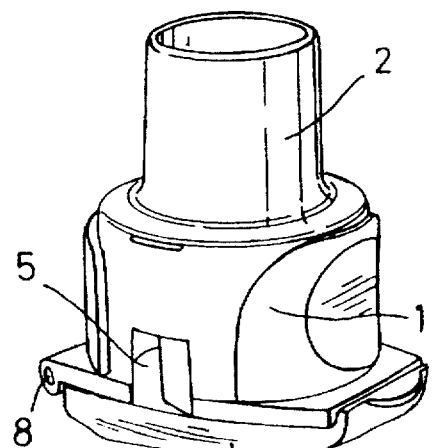
Figure 4:
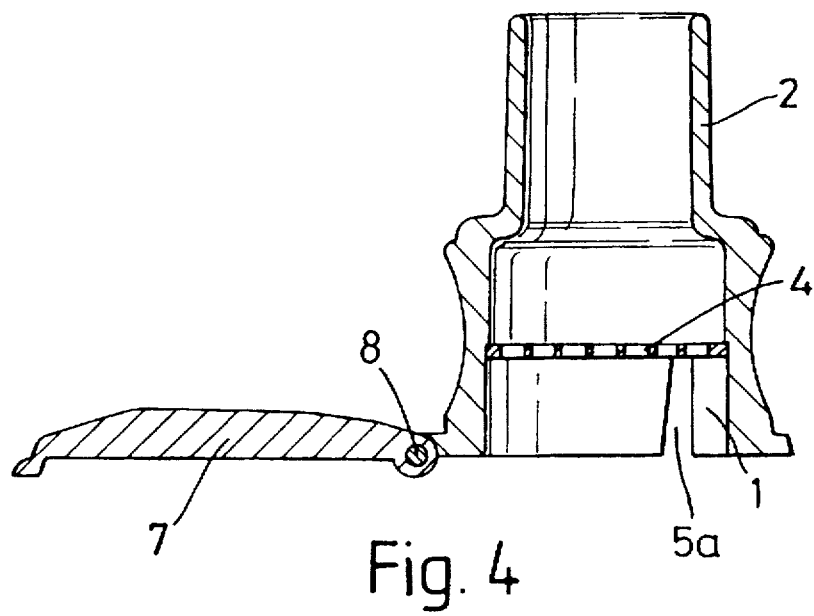
Figure 5:
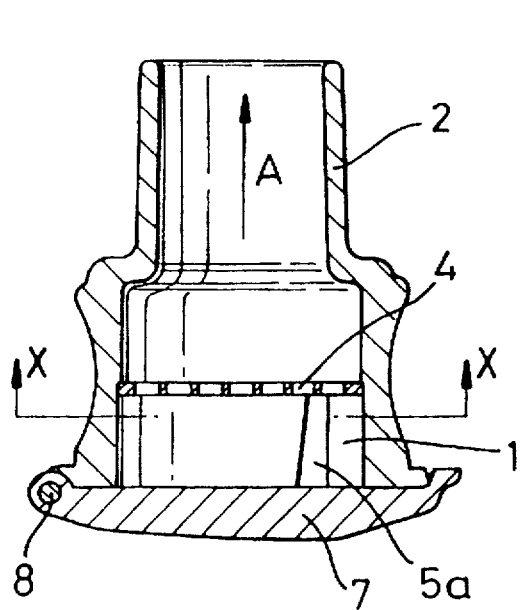
Figure 6:
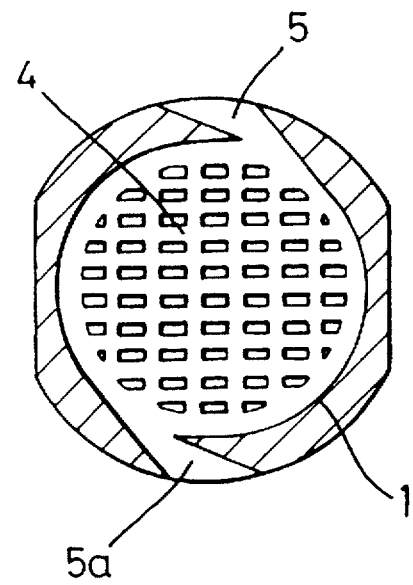

A preferred embodiment of the invention will now be described, by way of illustration only, with reference to the accompanying drawings, in which:

FIG. 1 is a perspective view of a device according to the invention with the mouthpiece cover in place, FIG. 2 is a perspective view of a device according to FIG. 1 with the mouthpiece cover removed, FIG. 3 is a side view of the device of FIG. 2, FIG. 4 is a longitudinal section of the device of FIG. 3 with cover open, and without the mouthpiece cover, FIG. 5 is the same longitudinal section of the device as in FIG. 4 but with cover closed, and FIG. 6 is a section along the line X—X of FIG. 5.

An inhalation device according to the invention comprises a generally cylindrical swirl chamber (1) adapted to receive a capsule (not shown) of powdered inhalation medicament having an aperture formed at each end. A mouthpiece (2), having a removable mouthpiece cover (3), extends from swirl chamber (1) and is separated therefrom by a grid (4). Two tangential air inlets (5, 5a) open into swirl chamber (1). When the mouthpiece cover (3) is in place on the device air inlets (5, 5a) are covered by extensions of the mouthpiece cover (6, 6a). The base of swirl chamber (1) remote from mouthpiece (2) is provided with a cover (7) having a continuous substantially planar inner surface, the cover (7) being attached to the base of the swirl chamber (1) via hinge (8), thus allowing access to the swirl chamber (1) for insertion and removal of a capsule. The end of the cover (7) remote from the hinge (8) is adapted to resiliently engage the base of the swirl chamber (1).

In use, cover (7) is opened and a capsule (not shown) of inhalation medicament having an aperture at each end is inserted into swirl chamber (1). Cover (7) is then closed and the mouthpiece cover (3) removed thus exposing air inlets (5, 5a). The patient inhales through mouthpiece (2), thereby drawing air through tangential air inlets (5, 5a) into swirl chamber (1). The air flowing into swirl chamber (1) causes the capsule to rotate thereby dispensing the medicament contained therein which is entrained into air flow (A) and inhaled by the patient. Once the medicament has been inhaled the mouthpiece cover (3) is replaced and cover (7) is opened to allow removal of the empty capsule.

I claim:

1. A device for the administration of powdered inhalation medicament contained initially in a medicament capsule having at least one aperture formed therein, said device comprising:

a swirl chamber adapted to receive the medicament capsule;

a mouthpiece communicating with the swirl chamber and separated therefrom by a grid;

at least one air inlet in tangential communication with the swirl chamber whereby air can be drawn through the device via the mouthpiece to cause a swirling air flow through the swirl chamber; and a cover member, having a continuous substantially planar inner surface, provided on the base of the swirl chamber remote from the mouthpiece;

said cover being moveable between a first position in which a medicament capsule can be inserted in the swirl chamber and a second position in which such a medicament capsule can be retained in the swirl chamber and rotated upon air being drawn through the device, thereby dispensing a medicament contained in such a medicament capsule;

said device having no capsule piercing means.

2. A device according to claim 1 wherein the cover member is in hinged engagement with the base of the swirl chamber.

3. A device according to claim 1 which has two air inlets in tangential communication with the swirl chamber.

4. A device according to claim 1 which is provided with a mouthpiece cover.

5. A device according to claim 4, wherein the mouthpiece cover is adapted to cover the mouthpiece and at least one air inlet communicating with the swirl chamber.

6. A device according to claim 5, wherein the mouthpiece cover is provided with at least one protruding element adapted to cover at least one air inlet.

7. A device as claimed in claim 1 in which a medicament capsule containing powdered inhalation medicament and having at least one aperture formed therein is retained in the swirl chamber.

8. A device as claimed in claim 1 wherein the at least one or each air inlet tapers towards the swirl chamber.

9. A device as claimed in claim 1 which has a plurality of air inlets spaced at regular intervals around the swirl chamber.

10. A method for administering a powdered inhalation medicament comprising:

inserting a capsule having at least one aperture formed therein and containing a powdered inhalation medicament into a device having a swirl chamber adapted to receive the medicament capsule, said device further having a mouthpiece communicating with the swirl chamber, the swirl chamber having an air inlet positioned tangentially to the swirl chamber and in communication with the mouthpiece, such that air drawn through the device via the mouthpiece creates a circumferential stream through the chamber which causes the capsule to rotate; and drawing an air stream through the swirl chamber in the direction of the mouthpiece causing the capsule to rotate in the swirl chamber and dispense the medicament contained through the aperture into the air stream and thence, into the mouthpiece;

said device having no capsule piercing means.

11. The method of claim 10 wherein the capsule is cylindrical.

* * * * *